(12) United States Patent
Beyersdorf et al.

(10) Patent No.: US 6,790,230 B2
(45) Date of Patent: Sep. 14, 2004

(54) VASCULAR IMPLANT

(75) Inventors: Friedhelm Beyersdorf, Freiburg (DE); Georg Lutter, Freiburg (DE)

(73) Assignee: Universitatsklinikum Freiburg, Freiburg (DE)

( * ) Notice: Subject to any disclaimer, the term of this patent is extended or adjusted under 35 U.S.C. 154(b) by 82 days.

(21) Appl. No.: 10/135,431

(22) Filed: Apr. 30, 2002

(65) Prior Publication Data

US 2002/0193871 A1 Dec. 19, 2002

(30) Foreign Application Priority Data

Apr. 30, 2001 (DE) .......................................... 101 21 210

(51) Int. Cl.[7] .............................. A61F 2/24; A61F 2/06
(52) U.S. Cl. ..................... 623/2.18; 623/1.3; 623/2.38
(58) Field of Search .................... 623/1.3, 1.31, 623/1.36, 900, 1.24, 1.26, 2.14, 2.17, 2.18, 2.38, 23.68, 23.7; 604/9

(56) References Cited

U.S. PATENT DOCUMENTS 6,458,153 B1 * 10/2002 Bailey et al. .............. 623/1.24

FOREIGN PATENT DOCUMENTS

| DE | 19546692 A1 | 6/1997 |
|---|---|---|
| DE | 10010074 A1 | 10/2001 |
| EP | 0592410 B1 | 10/1995 |

* cited by examiner

Primary Examiner—David H. Willse
(74) Attorney, Agent, or Firm—Volpe and Koenig, P.C.

(57) ABSTRACT

An anchoring element including a replacement heart valve for the purposes of intraluminal anchoring of the heart valve element to mammalian hearts, the anchoring element having a small enough initial volume prior to its placement that it can be brought to its point of use using a catheter through a blood vessel and can be expanded there to its functionally correct dimensions. The anchoring element is shaped differently from a cylindrical shape such that it is connected to the aorta at the point of use at least in areas in a form-locked manner. This facilitates an especially good seating of the anchoring element containing the replacement heart valve.

9 Claims, 2 Drawing Sheets

VASCULAR IMPLANT

BACKGROUND

This invention relates to an anchoring element containing a replacement heart valve for the purposes of intraluminal anchoring of the replacement heart valve to mammalian hearts, in particular human hearts. The anchoring element has a low enough initial volume prior to its placement, including the replacement heart valve, that it can be placed through a blood vessel to its point of use using a catheter and expanded there to its functionally correct dimensions. The invention also includes a process to manufacture the above anchoring element.

Whereas earlier, the replacement of heart valves had been done through open-heart surgery, EP 0 592 410 describes a heart valve anchoring device that can be placed into its correct position via a catheter without an open-heart operation. This heart valve anchoring device has a cylindrical tubular section as the anchoring element that extends in an essentially straight line to its point of use along a certain length of the aorta and contains the heart valve at its entrance (with respect to the direction of blood flow) or at another suitable position. Alternatively, and especially for the aorta, an anchor is described that consists of two meandering wires connected together and that has an overall circular shape. This is intended to make it possible to place a valve prosthesis into the aorta at three points, namely in the descending section of the aorta (pars descendens aortae), at a point between the coronary arteries and the left ventricle of the heart, or in the aorta at a point directly behind the mouth of the coronary arteries.

Because of its tubular or circular shape, however, the anchor that is achieved is inadequate or insufficient since this anchor must withstand blood flow under high pressure and high velocity, and with a lot of pulsation. The anchoring element could shift under this dynamic load. The result could be the blockage of one or even a number of discharging arteries, such as the coronary vessels. If, for example, a heart valve were to shift far enough that it were to lie against the outlets for the coronary vessels in the direction of blood flow, this could result in the death of the patient.

SUMMARY

Thus, the object is to provide an anchoring element of the type mentioned above whose shift within the aorta away from its point of use is prevented despite high dynamic loads, even at high physical exertion levels, such as in sports.

To meet this object, an intraluminal anchoring element provided with a replacement heart valve is shaped, in deviation from the cylindrical form, such that it is connected in a form-locked manner to the aorta, at least in places, at its point of use.

An intraluminal anchoring element of this type is called simply an "anchoring element" below.

This invention thus takes advantage of the aorta itself having shapes and contours that themselves deviate from the cylindrical shape. For example, the aorta has at the outlet of the heart, directly behind the original aortic valve, so-called bulbi, and further on (especially in the arcus aortae) has a significant bend. Also, vessel outlets exist at which the wall of the aorta is necessarily interrupted.

It is therefore useful for the shape of the anchoring element at the point of use located at the heart outlet (behind the original aortic valve) to have a widening section extending in the radial direction.

It is also advantageous if the anchoring element is tailored to the interior shape of the bulbi and/or has a curved contour to fit the interior shape of the aorta and its curved contour, in particular if the anchoring element lines the aorta.

An anchoring element of this type no longer shifts after being properly installed at the point of use, not even in the direction of the strong pulsating blood flow. Moreover, it is then connected in a form-locked manner to the aorta from the inside.

Another improvement in the anchoring of the anchoring element can be achieved by providing it with a projection that is permeable to blood (i.e. provided with a cut-out or opening), in particular a circular projection near at least one arterial outlet (arterial branch), for example near one or more outlets selected from those for the coronary vessels and those that supply arterial blood to the head and/or arms. This projection lies against the initial section of the wall of the respective discharging artery at the point of use, preferably form-locked to the wall.

It is simply the shape of the anchoring element according to the invention, which differs from the cylindrical shape, that prevents not only shifting, but also rotation, so that particularly the lateral openings for the outlets also remain in their correct position even if there are no projections provided that extend into the outlets.

To further improve the seating, the exterior of the anchoring element is profiled, in particular there are small projections on the exterior of the anchoring element, for example, in the form of small teeth, spines or peaks. This provides an additional anchoring to the wall of the aorta, and thus an especially solid seating.

A preferred variation of all anchoring elements mentioned above and to follow has the dimensions and length corresponding to the aorta from the area of the bulbi up to at least the outlet (ostium) for the truncus brachiocephalicus, preferably up to the outlet for the arteria carotis communis sinistra, above all up to just before the outlet of the arteria subclavia sinistra.

The anchoring element is preferred to be constructed essentially of thread-like structures (filaments) that, for example, are latticed, looped, or wound and/or of closed structural elements having suitable cut-outs, for example for the ostia. It can include, in particular, a number of meandering thread-like structures, each of which forms a ring, and can have additional specifically bent (for example around the ostia) thread-like structures. The thread-like structures form a ring and, if necessary, the specifically bent thread-like structures are connected among themselves and/ or together by means of other thread-like structures (for example by adhesion, soldering, welding or direct integration, for example by casting from forms). This allows it to be compressed or pushed together (volume reduction) so that it can be introduced into the feed tube or catheter. The thread-like structure can be made of fine stainless steel or titanium or similar metals or metal alloys, or of suitable plastics.

It is preferred that any blood vessel outlets (arteries) lying near the anchoring elements (in addition to the openings at the two terminal ends), such as the outlets of one or both coronary vessels, the truncus brachiocephalicus, the arteria carotis communis sinistra or the arteria subclavia sinistra, or outlets of more than one of these if they lie near the anchoring element, remain open—this is preferred to be accomplished by appropriate cut-outs (openings), in particular over the ostia for the coronary arteries. This will prevent obstructions to blood flow, for example due to turbulence around the thread-like structures or partial closing of the ostia and/or it will minimize the danger of the formation of thromboses.

Preferably, the anchoring element should be made of a material that is capable, either due to its elasticity or due to its shape memory, or both, of guaranteeing self-expansion to its final shape after it is installed using the catheter. It should then have sufficient rigidity to keep its shape.

It is especially preferred that at least the shaping components of the anchoring elements be made of a shape-memory material, preferably of shape-memory polymers and/or of memory metal (shape-memory alloys), such as copper/zinc/aluminum, copper/aluminum/nickel or in particular nickel/titanium shape-memory alloys, and above all those with one-way effects (in this case the alloy re-assumes its earlier shape only when it exceeds its critical temperature, and retains this shape even after again falling below the critical temperature). It is preferred to select this memory metal such that the critical temperature is below body temperature so that the expansion to its final shape is caused by the temperature in the body (i.e., in the patient, when the anchoring elements containing the valve is introduced). In an especially preferred embodiment of the invention, at least the shape-determining components of the anchoring elements are made of a memory metal, in particular Nitinol (a corrosion-resistant, highly rigid titanium/nickel shape-memory alloy that is elastically deformable up to approximately 8%; this can be obtained from Nitinol Devices & Components Inc., Fremont, USA, for example).

In some preferred embodiments, these shaping elements can, as can other components, for example the entire anchoring element, be layered with cells or coatings of thin cellular tissues. These cells are preferred to be obtained from the actual cells of the respective patient's body, or are pre-treated cells from other humans or animals. The elements can also be layered with other biocompatible materials, such as plastics.

An especially good anchoring and an especially effective form-lock to the inner wall of the aorta can be achieved if the anchoring element's individual spatial coordinates are essentially the same as those of the aortic lumen of the respective patient.

To this end an assortment of various sized and/or shaped anchoring elements can be used. It is then only necessary to select the right pattern that best fits the spatial coordinates of the patient.

It is then prepared after measuring the spatial coordinates or the respective patient.

This invention also pertains to a method or a process to manufacture or preform an anchoring element as described above or in the following according to the individual anatomical ratios of the respective patient, said process characterized in that the spatial coordinates (i.e. the contour, position and shape of the bulbi, position and shape of the arterial outlets, above all the shape of the boundaries of the cavity region) of the aorta are measured and that the anchoring element is manufactured using the dimensions and shapes (individual) determined in this manner.

To perform the measurements, particularly suitable processes are visual processes that can penetrate the body tissue. This allows the measurements of a patient to be done without requiring additional surgical or other medical treatment.

Especially precise measurement results (spatial coordinates) can be obtained through computer tomography (CT), in particular spiral computer tomography or 3D computer tomography, including difference methods (comparison before and after contrast medium administration), such as using subtraction angiography (intraarterial, for example), or using nuclear spin resonance tomography (NMR tomography). Also, positron electron tomography, 3D scintigraphy or similar methods can be used.

Based on the spatial coordinates obtained in this way, the anchoring device is manufactured in a conventional manner accordingly.

The resultant slight increase in work to manufacture the anchoring elements with dimensions differing slightly from one to another is offset by the considerable improvement in the anchoring in each patient since any risk should be eliminated as much as possible for that patient.

A special embodiment also pertains to an anchoring element that can be manufactured with the above process (determination of the spatial coordinates of the aorta, in particular its interior wall, also in particular the bulbi and/or the arterial outlets, and then the manufacture of the correctly shaped anchoring element or the same with attached valve replacement).

As a valve replacement, a plastic or, preferably, biological valve material is used that can be attached to a sufficiently small volume (for example by rolling and/or folding). Suitable valve materials from animals with valves of equivalent size, such as pigs, or from deceased persons, are suitable biological materials, as are valves created from the [patient's own] pericardium or from a pericardium originating from animals or deceased persons. These valves can be fixed using glutaraldehyde (0.6%) for example, and can be provided with an ultra-thin polytetrafluoroethylene layer for stabilization. The replacement valve is sutured to the interior of the anchoring element according to the invention using common stitches made of materials that remain permanently in the body, such as 7-0 polypropylene, preferably terminal at the end of the blood influx. Prior to implantation, the anchoring element containing the valve replacement is fixed in a suitable manner, for example in a buffered physiological saline solution containing 0.6% glutaraldehyde for 24 hours at 4° C.

The anchoring element with the valve replacement attached to it can then be transferred to the correct position in the aorta by means of a catheter, for example through the arteria iliaca, the infrarenal aorta, or the femoral artery and opened up there. The expansion to its final shape then takes place based on the prescribed shape, mainly as a result of elastic forces and/or forces based on shape-memory. Especially when using materials with shape-memory effects, and because of prescribing the shape in a preferred embodiment of the invention, there is no need for an expanding balloon that can damage the valve replacement under certain circumstances.

The anchoring elements according to the invention are particularly suited for those patients in which the wall of the aorta near the aorta ascendens, the arcus aortae and at the beginning of the aorta descendens exhibits little or no elasticity or exhibits narrowing (stenoses), i.e. mainly older patients. They are therefore also especially suited for those patients for whom open-heart operations are not recommended due to their condition as a result of age.

If necessary, suppression of the immune system common in transplantation medicine must be done to prevent rejection reactions in the patient when the valve replacement comes from other animals (xenotransplantation), for example using immunosuppressors like Cyclosporin.

BRIEF DESCRIPTION OF THE DRAWINGS

Below, a preferred embodiment of the invention is described in more detail with the aid of the appended drawings. This preferred embodiment serves to illustrate the invention and shows especially preferred embodiments of the invention, but is not intended to limit the scope thereof.

In the drawings, shown in schematic form in some areas are.

DETAILED DESCRIPTION OF THE PREFERRED EMBODIMNENT

Figure 1:
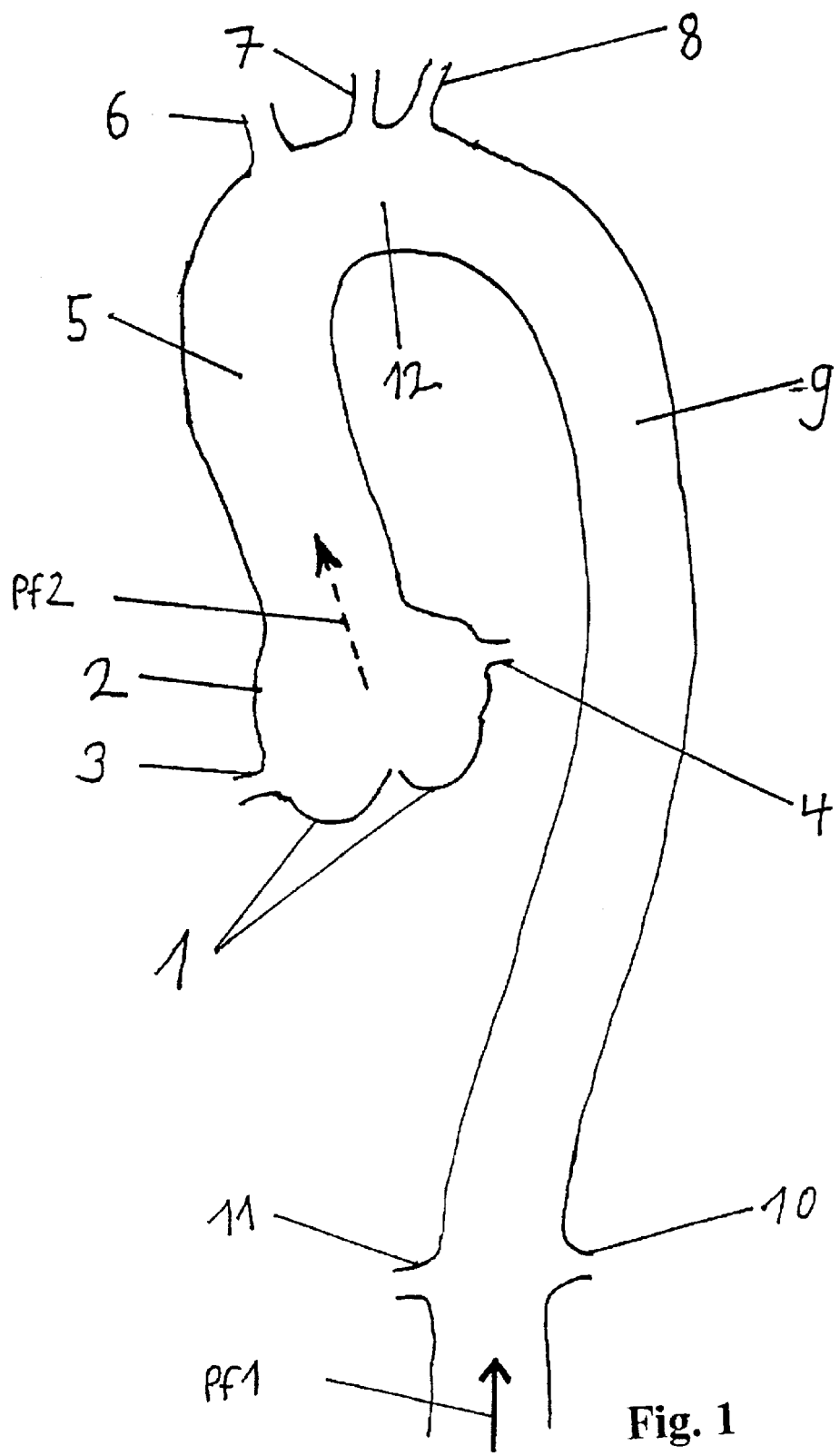
FIG. 1 is a schematic representation of the human aorta in a longitudinal section.

In FIG. 1, two of the three valves 1 of the aortic valve are shown, along with one of the bulbi 2; the branch 3 (ostium) of the arteria coronaria dextra, the arteria coronaria sinistra 4; the pars ascendens of the aorta 5; the branch of the truncus brachiocephalicus 6 (arterial branch to supply the right arm and the right arteria carotis); the branch of the arteria carotis communis sinistra 7 (left jugular vein); the branch of the arteria subclavia sinistra (which mainly supplies the left arm) 8; the pars descendens of the aorta 9; distal arterial branches 10 and 11 are schematically indicated; and the arcus aortae 12. The solid arrow Pf1 shows an example of the path of a catheter to implant an anchoring element according to the invention. The dashed arrow Pf2 indicates the normal direction of blood flow.

Figure 2:
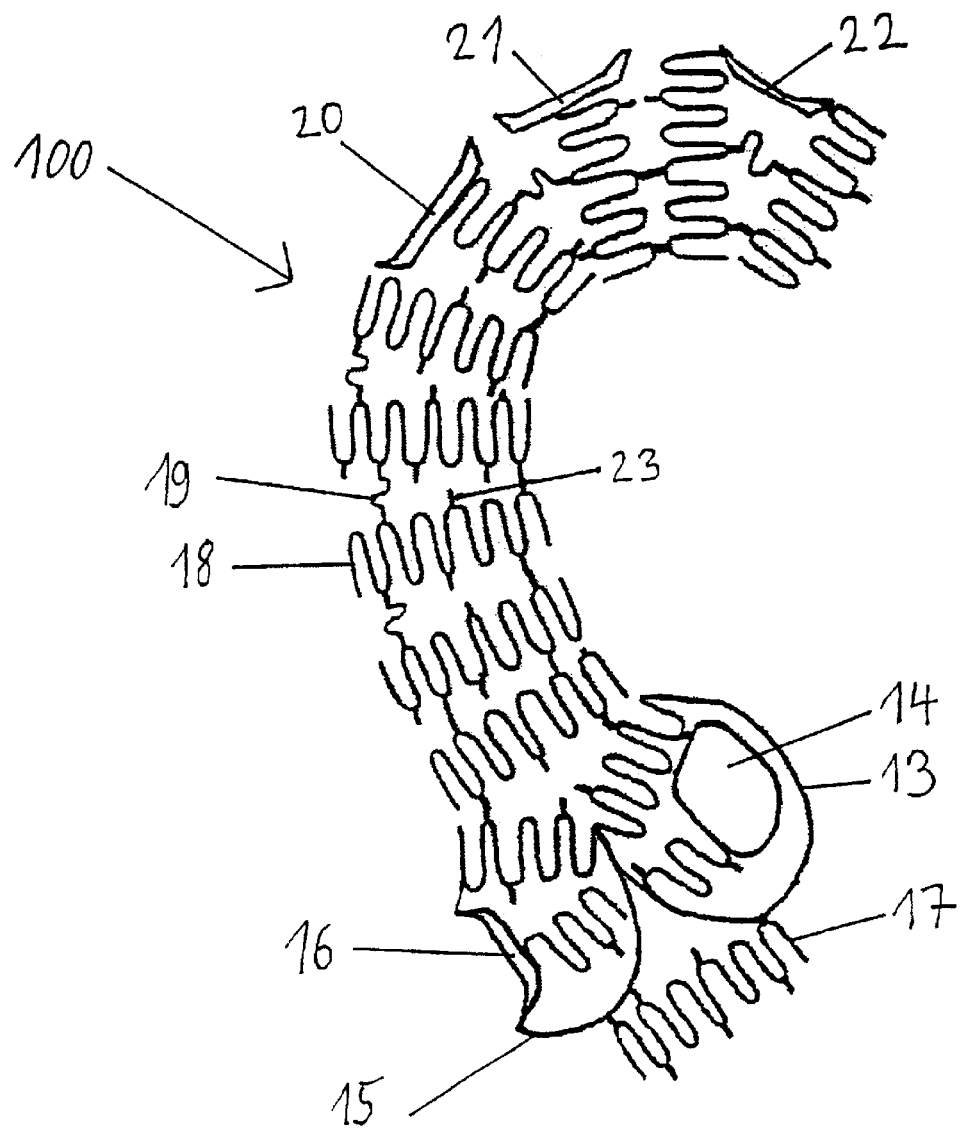
FIG. 2 is a schematic view of the anchoring element in accordance with the invention.

FIG. 2 shows an anchoring element 100 in schematic form, here without a valve replacement. Directly at the point or near the point of the original heart valve is a circular element 17, here made of meandering Nitinol wire. This is used to attach a replacement heart valve (not shown here), for example taken from a pig. In the direction of blood flow there is then an area with expansions for the left front bulbus 13 with an opening 14 for the arteria coronaris sinistra and for the right front bulbus 15 with an opening 16 for the arteria coronaris dextra. Another circular element 18 is shown, for example, in the contour of the aorta ascendens, with the individual circular elements being connected using connecting wires such as 19. A spine-shaped protrusion 23 facing the outside of the anchoring element that is used to further stabilize the position in the aorta. An opening 20 for the ostium of the truncus brachiocephalis, an opening 21 for the ostium of the arteria carotis communis sinistra and an 22 opening for the ostium of the arteria subclavia sinistra are also shown. The anchoring element (here designed as a stent) is made of a Nitinol wire and is shown in its expanded form as would occur in the aorta after complete installation. The drawing combines all of the special advantageous features contributing to an especially good and safe seating of the anchoring element and to keep free the branching vessel ostia.

To obtain a valve replacement made of biological material and to fix it to the anchoring element, the following procedure can be used, for example: a foldable heart valve is manufactured by attaching an aortic valve from the heart of a recently slaughtered pig. The aortic valve is carefully cut to size (after transporting it in 70% ethanol), to reduce the profile, hanging tissue is removed, and it is cleaned by hand. The valve is then correctly dimensioned (in correlation with the diameter of the aorta as determined through intraarterial subtraction angiography) and attached to the interior of the circular element (17) shown in example 1 by stitching with 7-0 polypropylene. Finally, the anchoring element with the valve replacement is wetted with a buffered physiological saline solution containing 0.6% glutaraldehyde. After fixing, the anchoring element with the valve replacement is transported in a 70% ethanol solution for further storage.

The resultant anchoring element 100 containing the valve replacement can then be volume-reduced and kept in a catheter administration system, for example. The positioning of the tubulus structure can then be done directly, possibly while monitoring using visual systems or using optical systems inside the catheter, by administering it through the arteria iliaca (from the direction of the solid arrow in FIG. 1).

The manufacture of an anchoring element (100) individual to the patient with an attached valve replacement is done as follows:

The spatial coordinates of the bulbi, the ostia for the coronary vessels, the pars ascendens and the aortic curve up to the beginning of the pars descendens of the aorta are measured, in addition to the outlets for the three arterial outlets in the arcus aortae, using NMR tomography or spiral CT. The spatial coordinates are used to manufacture an anchoring element 100 as shown in FIG. 2. As described above, an aortic valve replacement is attached to this anchoring element that is tailored to the patient's data. This yields an anchoring element with an aortic valve replacement that is fit optimally to the inner aortic lining of the patient and is thus suited for very good seating.

What is claimed is:

1. An anchoring element of a replacement heart valve for intraluminal anchoring of the replacement heart valve to mammalian hearts, the anchoring element comprises a low enough initial volume prior to its placement that it can be placed through a blood vessel to its point of use using a catheter and expanded there to its functionally correct dimensions, wherein the anchoring element is shaped in a deviation from a cylindrical form, such that it is configured to be connected in a form-locked manner to the aorta at a point of use;

comprises a widening section configured to extend in a radial direction at the point of use at a heart outlet; and is tailored to an interior shape of the bulbi and has a curved contour to fit an interior shape of the aorta and its curved contour.

2. An anchoring element according to claim 1, further comprising cutouts for arterial outlets located near the anchoring element.

3. An anchoring element according to claim 1, further comprising a profiled exterior having at least one of small teeth, spines or peaks.

4. An anchoring element according to claim 1, wherein the anchoring element has dimensions and length corresponding to the aorta from an area of the bulbi up to at least an outlet for the truncus brachiocephalicus.

5. An anchoring element according to claim 1, including a number of meandering thread-like structures forming a ring, said thread-like structures being connected among themselves through other thread-like structures.

6. An anchoring element according to claim 1, wherein the anchoring element has a protrusion permeable to blood near at least one arterial outlet, the protrusion is adapted to sit against a beginning section of a wall of a respective discharging artery at the point of use.

7. An anchoring element according to claim 1, comprising a shape-memory material, including at least one of a shape-memory polymer or a memory metal.

8. An anchoring element according to claim 7, wherein the anchoring element is made of a memory metal that is a nickel/titanium shape-memory alloy.

9. An anchoring element according to claim 1, wherein the anchoring element has individual spatial coordinates essentially the same as that of an aortic lumen of the respective patient.

* * * * *